(12) United States Patent
Goodson

(10) Patent No.: US 10,463,582 B2
(45) Date of Patent: Nov. 5, 2019

(54) SHAVING FORMULATION AND METHOD OF USE THEREOF

(71) Applicant: Mark Goodson, Columbia, SC (US)

(72) Inventor: Mark Goodson, Columbia, SC (US)

(73) Assignee: Mark Goodson, Columbia, SC (US)

( * ) Notice: Subject to any disclaimer, the term of this patent is extended or adjusted under 35 U.S.C. 154(b) by 0 days.

(21) Appl. No.: 15/558,586

(22) PCT Filed: Mar. 17, 2016

(86) PCT No.: PCT/US2016/022812
§ 371 (c)(1),
(2) Date: Sep. 15, 2017

(87) PCT Pub. No.: WO2016/153909
PCT Pub. Date: Sep. 29, 2016

(65) Prior Publication Data
US 2018/0055743 A1    Mar. 1, 2018

Related U.S. Application Data

(60) Provisional application No. 62/206,009, filed on Aug. 17, 2015, provisional application No. 62/135,814, filed on Mar. 20, 2015.

(51) Int. Cl.
| | | |
|---|---|---|
| *A61K 8/04* | (2006.01) | |
| *A61K 8/36* | (2006.01) | |
| *A61K 8/31* | (2006.01) | |
| *A61K 8/89* | (2006.01) | |
| *B05B 11/00* | (2006.01) | |
| *B05B 15/00* | (2018.01) | |
| *A61Q 9/02* | (2006.01) | |
| *A61K 8/97* | (2017.01) | |
| *A61K 8/9789* | (2017.01) | |
| *B05B 15/30* | (2018.01) | |
| *A61K 8/34* | (2006.01) | |
| *A61K 8/42* | (2006.01) | |

(52) U.S. Cl.
CPC ............... *A61K 8/046* (2013.01); *A61K 8/31* (2013.01); *A61K 8/34* (2013.01); *A61K 8/345* (2013.01); *A61K 8/361* (2013.01); *A61K 8/42* (2013.01); *A61K 8/89* (2013.01); *A61K 8/97* (2013.01); *A61K 8/9789* (2017.08); *A61Q 9/02* (2013.01); *B05B 11/3053* (2013.01); *B05B 15/30* (2018.02); *A61K 2800/48* (2013.01)

(58) Field of Classification Search
CPC . A61K 8/046; A61K 8/31; A61K 8/36; A61K 8/89; B05B 11/3053; B05B 15/005
See application file for complete search history.

(56) References Cited

U.S. PATENT DOCUMENTS

| | | | |
|---|---|---|---|
| 5,252,331 A | 10/1993 | Curtis et al. | |
| 6,581,807 B1 | 6/2003 | Mekata | |
| 8,486,463 B1* | 7/2013 | Brieva | A61K 8/97 424/725 |
| 8,844,843 B2* | 9/2014 | Horiuchi | B05B 1/3436 239/468 |
| 2008/0233060 A1* | 9/2008 | Grune | A61K 8/27 424/59 |
| 2011/0226272 A1 | 9/2011 | Focht et al. | |

FOREIGN PATENT DOCUMENTS

| | | |
|---|---|---|
| DE | 10 2013 219 980 A1 | 4/2014 |
| WO | 9107943 A1 | 6/1991 |
| WO | 2011103449 A2 | 8/2011 |
| WO | 2014201541 A1 | 12/2014 |

OTHER PUBLICATIONS

International Search Report for PCT/US16/22812 dated Jun. 9, 2016 (2 pages).
Written Opinion for PCT/US16/22812 dated Jun. 9, 2016 (7 pages).

* cited by examiner

*Primary Examiner* — Mina Haghighatian
(74) *Attorney, Agent, or Firm* — Shumaker, Loop & Kendrick, LLP

(57) ABSTRACT

Disclosed is a shaving formulation having sesame oil, olive oil, sandalwood oil, broccoli oil, or any combination thereof, which allows for a smooth, non-irritating shave. The disclosed composition is preferably either an aqueous solution or a lotion that does not build up on the skin and preferably has moisturizing, healing, and/or anti-inflammatory properties that prevent or reduce the occurrence of dry skin, irritated/inflamed skin, in-grown hairs, or any combination thereof The disclosed shaving formulations preferably further include anti-microbial properties, anti-septic properties, or any combination thereof. The disclosed shaving formulations have a low viscosity such that the formulations may be applied from spray bottle or a container equipped with an atomizing head in the form of a mist onto a desired bodypart.

7 Claims, 2 Drawing Sheets

SHAVING FORMULATION AND METHOD OF USE THEREOF

CROSS REFERENCE TO RELATED APPLICATIONS

This U.S. National Application claim priority from PCT/US2016/022812filed Mar. 17, 2016, which claims priority from U.S. Provisional Patent Application No. 62/135,814 filed on Mar. 20, 2015 and U.S. Provisional Patent Application No. 62/206,009 filed on Aug. 17, 2015, each of which are incorporated by reference in their entirety.

TECHNICAL FIELD

The present invention relates generally to the field of personal hygiene and cosmetics, and more particularly, relates to novel shaving formulations and methods of use thereof.

BACKGROUND OF THE INVENTION

Many believe that shaving facial hair and/or body hair provides a more aesthetically appealing look. Thus, it is commonplace for men to shave facial hair and for women to shave their legs and underarms to achieve this desired aesthetic look.

Over time, numerous shaving formulations have been made to aid with shaving and to make this practice more tolerable and enjoyable. Conventional shaving creams often contain alcohols, oils, and various detergents. For example, many conventional shaving formulations are foaming shaving creams that are dispensed as a thick, viscous cream or foam. The objective of most conventional shaving creams is to provide for quick and efficient dispensing coupled with providing a moderate to robust lather. This combination of features allows a user to shave a desired body part. However, due to the inclusion of various alcohols and detergents (e.g., sodium lauryl sulfate) in conventional shaving creams, these conventional shaving creams often irritate a user's face, which may lead to dry skin, irritated/inflamed skin, in-grown hairs, or any combination thereof.

Also, most shaving creams having moderate to robust lathering irritate the skin due their high viscosity. More specifically, shaving creams having moderate to robust lathering tend to be highly viscous, and when applied to a user's face, the user must apply great force to the razor to shave. This great force subsequently creates acute physical trauma by pulling hair, irritating hair follicles, and creating micro-shear forces against the skin, thus resulting in dry skin, irritated/inflamed skin, and in-grown hairs.

BRIEF SUMMARY OF THE INVENTION

Therefore, a need exists to overcome the disadvantages of current shaving formulations. Disclosed is a shaving composition that allows the razor to glide over a user's face and/or body, thus providing a smooth, non-irritating shave. The disclosed formulation may be an aqueous liquid or a cream, e.g. a lotion, that does not build up on the skin. These formulations preferably have moisturizing, healing, and/or anti-inflammatory properties that prevent or reduce the occurrence of dry skin, irritated/inflamed skin, and in-grown hairs. The disclosed shaving formulation preferably further includes anti-microbial properties, anti-septic properties, or any combination thereof. The disclosed shaving formulation is preferably a sprayable shaving formulations that may be applied via a spray bottle and/or atomizing head in the form of a mist and/or aerosol to the face or desired bodypart.

In certain aspects, the disclosed shaving formulation may include from 5 to 60 wt % of at least one fatty acid or salt thereof; at least one of sesame oil from 0 to 20 wt %, olive oil from 0 to 10 wt %, sandalwood oil from 0 to 10 wt %, broccoli seed oil from 0 to 10 wt %, or a combination thereof; 1 to 10 wt % water; 0 to 20 wt % of a petroleum based lubricant, 0 to 20 wt % of a silicone based lubricant; 0 to 5 wt % fragrance, 0 to 5 wt % preservative, 0 to 5 wt % antimicrobial agent, or any combination thereof. In certain aspects, the shaving formulation is an aqueous solution having low viscosity so that it may be dispensed from a container having either a spray pump or an atomizing head.

Also disclosed is a method of dispensing the disclosed shaving formulation by providing a spray pump bottle or a container having an atomizing head containing the shaving formulation; dispensing the shaving formulation onto a desired surface (e.g., the face, legs, or other desired body part); and removing the shaving formulation from the desired surface by shaving the desired surface with a razor. In certain aspects, the spray pump bottle is configured to spray a mist of the shaving formulation onto the user's skin.

Embodiments of the invention can include one or more or any combination of the above features and configurations. Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION OF THE INVENTION

Figure 1:
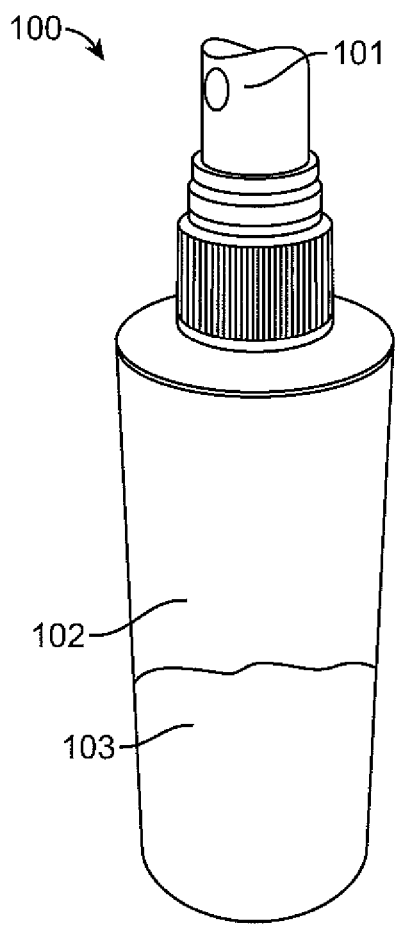
FIG. 1 depicts a spray pump bottle containing the shaving formulation that is configured to apply the shaving formulation as a mist.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting. In addition, the present invention will now be described more fully hereinafter with reference to the accompanying drawings in which exemplary embodiments of the invention are shown. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention. Like reference numbers refer to like elements throughout the various drawings.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a surfactant" includes mixtures of two or more such surfactants, and the like.

"Optional" or "optionally" means that the subsequently described event or circumstance can or cannot occur, and that the description includes instances where the event or circumstance occurs and instances where it does not. For example, the phrase "optional fragrances" means that a fragrance may or may not be present in the compositions described herein.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Disclosed is a shaving formulation that allows the razor to glide over a user's face and/or body. The disclosed formulation preferably is a lotion or aqueous solution (e.g., an water in oil emulsion or oil in water emulsion) that does not build up on the skin and has moisturizing, healing, and/or anti-inflammatory properties that prevent or reduce the occurrence of dry skin, irritated/inflamed skin, or in-grown hairs often associated with shaving. The disclosed shaving formulations preferably further include anti-microbial properties, anti-septic properties, or any combination thereof. The disclosed shaving formulations may be applied via a spray bottle or container having an atomizing head in the form of a mist to the face or desired bodypart.

According to the present invention, the disclosed shaving formulations include:
  (a) from 5 to 80 wt % of at least one fatty acid or salt thereof;
  (b) at least one of sesame oil from 2 to 20 wt %, olive oil from 0 to 10 wt %, sandalwood oil from 0 to 10 wt %, broccoli seed oil from 0 to 10 wt %, or a combination thereof;
  (c) 1 to 10 wt % water;
  (d) 0 to 20 wt % petroleum based lubricant, 0 to 20 wt % of a silicone based lubricant, 0 to 5 wt % fragrance, 0 to 5 wt % preservative, 0 to 30 wt % alcohol, 0 to 10 wt % thickeners, and 0 to 5 wt % antimicrobial agent; and
  (e) any combination of (a)-(e).

The consistency of the shaving formulations can include a paste or pasty substance, a cream, a lotion, or an aqueous, non-viscous liquid. In certain preferred aspects, the shaving formulation is either a lotion or an aqueous, non-viscous liquid capable of forming a mist when dispensed from a spray pump bottle or from a bottle having an atomizing head. The disclosed formulations preferably have a viscosity of 3 to 500 cP, 3 to 100 cP, 3 to 75 cP, 3 to 40 cP, 3 to 10 cP, 3 to 5 cP at a temperature ranging from 65° F. to 100° F., from 70° F. to 85° F., and from 72° F. to 80° F.

The shaving formulations preferably include at least one of sesame oil, olive oil, sandalwood oil, broccoli seed oil, or a combination thereof because of their desired anti-inflammatory and skin moisturizing properties. These anti-inflammatory properties may include, but are not limited to, antioxidant characteristics in which free radicals are bound and sequestered to prevent or limit skin irritation associated with shaving and shaving induced inflammation. In certain aspects, sesame oil is included within the shaving formulation at a concentration ranging from 2 to 20 wt %, 3 to 15 wt %, 4 to 12 wt %, or 5 to 9 wt % of the overall weight of the shaving formulation. In certain aspects, the sesame seed oil is 98% pure, 99% pure, or pharmaceutical grade purity (e.g., 99.9% pure). In certain aspects, olive oil is included within the shaving formulation at a concentration ranging from 0 to 10 wt %, 1 to 10 wt %, 2 to 9 wt %, 2 to 8 wt %, 3 to 8 wt %, 3 to 7 wt %, 4 to 7 wt %, or 4 to 6 wt % of the overall weight of the shaving formulation. In certain aspects, the olive oil is 98% pure, 99% pure, or pharmaceutical grade purity (e.g., 99.9% pure). In certain aspects, sandalwood oil (e.g., derived from *Santalum Album, Santalum Ellipticum, Santalum Spicatum*, or any combination thereof) is included within the shaving formulation at a concentration ranging from 0 to 10 wt %, 1 to 10 wt %, 2 to 9 wt %, 2 to 8 wt %, 3 to 8 wt %, 3 to 7 wt %, 4 to 7 wt %, or 4 to 6 wt % of the overall weight of the shaving formulation. In certain aspects, the sandalwood oil is 98% pure, 99% pure, or pharmaceutical grade purity (e.g., 99.9% pure). Sandalwood oil may be preferably included within the shaving formulation because of its antiseptic and anti-inflammatory properties coupled within its desirable sent. Thus, when included within the shaving formulations, sandalwood oil may decrease the occurrence of in-grown hairs and may further prevent or reduce the occurrence of dry skin. Broccoli seed oil may also be included within the shaving formulation at a concentration ranging from 0 to 10 wt %, 1 to 10 wt %, 2 to 9 wt %, 2 to 8 wt %, 3 to 8 wt %, 3 to 7 wt %, 4 to 7 wt %, or 4 to 6 wt % of the overall weight of the shaving formulation. In certain aspects, the broccoli seed oil is 98% pure, 99% pure, or pharmaceutical grade purity (e.g., 99.9% pure). Broccoli seed oil is unique in the fact that it has excellent absorption properties and can re-vitalize keratin (e.g., skin and hair). It is further beneficial because of its anti-oxidant properties, which may prevent an inflammatory response during and/or after shaving.

In certain aspects, the shaving formulations include at least one fatty acid or salts thereof, including various surfactants discussed below. These fatty acids can be linear or branched glycerides including, for example, saturated monoglycerides. For example, these fatty acids and/or fatty acid salts may include, but are not limited to, stearic acid and derivatives thereof, palmitic acid and derivatives thereof, arachidonic acid and derivatives thereof, oleic acid and derivatives thereof, linolenic acid and derivatives thereof, myristic acid and derivatives thereof, or any combination. One or more of these fatty acids may be present in the disclosed formulations at a concentration of 5 to 80 wt %, 60 to 80 wt %, 70 to 80 wt %, 5 to 60 wt %, 10 to 55 wt %, 10 to 45 wt %, 20 to 60 wt %, 20 to 55 wt %, 40 to 60 wt %, or 50 to 60 wt % of the overall concentration of the disclosed formulation. Salts of the fatty acids employed herein may be prepared by reacting, for example, the above mentioned acids by known conventional condensation processes. Illustrative of such salts are alkali, alkaline earth, ammonium, and in particular, the sodium, potassium, and calcium salts of fatty acid esters wherein the fatty acid contains 14 to 22 carbon atoms. The saturated monoglycerides useful in the present invention have an iodine value of 0 to about 20. Preferred saturated monoglycerides include those having iodine values of 0 to about 5, those made by inter-esterification of glycerine with fully saturated fats or oils such as tallow, palm oil, cottonseed oil, soybean oil, peanut oil, sesame oil and the like. These monoglycerides usually contain monoesters at a concentration of at least 90% by weight. Alternatively, such monoglycerides can be prepared by reacting glycerine with straight chain fatty acids such as those found in vegetable oils and animal fats having from about 8 to about 22 carbon atoms, and saturated to an extent to result in an iodine value of about 0 to about 5. Such monoglycerides are commercially available, for example, Myverol® 18-00, 18-04, 18-06 and 18-07 distilled monoglycerides, products of Eastman Chemicals Products. Inc. Particularly preferred fatty acids are stearic acid and derivatives thereof and myristic acid and derivatives thereof, including but not limited to, stearic acid at a concentration ranging from 1 to 60 wt %, 2 to 30 wt %, 2 to 10 wt %, 3 to 7 wt %, or 3 to 5 wt % of the overall concentration of the formulation, glycol stearate at a concentration ranging from 1 to 50 wt %, 2 to 30 wt %, 2 to 15 wt %, 4 to 10 wt %, 5 to 10 wt %, or 6 to 9 wt % of the overall concentration of the formulation, isopropyl isostearate ranging from 1 to 50 wt %, 2 to 30 wt %, 2 to 15 wt %, 4 to 10 wt %, 5 to 10 wt %, or 6 to 9 wt % of the overall concentration of the formulation, isopropyl myristate ranging from 1 to 60 wt %, 2 to 30 wt %, 2 to 10 wt %, 3 to 7 wt %, or 4 to 6 wt % of the overall concentration of the formulation, and glyceryl stearate ranging from 1 to 60 wt %, 2 to 30 wt %, 2 to 10 wt %, 3 to 7 wt %, or 4 to 6 wt % of the overall concentration of the formulation. In certain aspects, triethanolamine, NaOH, KOH, or any combination thereof may be further included within the formulation to aid in neutralization of the disclosed fatty acids, thus providing a pH balanced formulation.

In certain aspects, isopropyl isostearate may be used as a skin conditioning agent and humectant thereby aiding in water retention of the user's skin and providing for a smooth feeling and soft silky appear post-shaving with the disclosed formulation. In certain aspects, glycol stearate may be used for its hair relaxing properties couple with its ability to provide a smooth and soft feeling to a user post-shaving with the disclosed formulation. Similar to isopropyl isostearate and glycol stearate, isopropyl myristate may be used because it provides a smooth and soft feeling to a user post-shaving. Isopropyl myristate may also be used because of its thickening characteristics, thereby aiding in achieving the desired viscosity of the formulation, while simultaneously and advantageously reducing or eliminating a "greasy" feeling or sensation on the user's skin. Glyceryl stearate may be used within the disclosed formulations as a lubricant on the user's skin. It easily penetrates the skin acting as a humectant to slow the loss of water by forming a barrier on the surface of the user's skin while concurrently protecting skin from free-radical damage as well. In certain aspects, glyceryl stearate may be included to stabilize the formulation and potentially make the formulation freeze-resistant.

In certain aspects, the disclosed formulations utilize one or more lubricants including, but not limited to, an organic, carbon based lubricant, a silicone based lubricant, or combinations thereof. Examples of organic, carbon based lubricants may include mineral oils, which may include, but are not limited to, alkane based oils having, preferably, ranging from $C_{15}$ to $C_{40}$ in length (e.g., $C_nH_{2n+1}$). In certain aspects, the mineral oils are petroleum based distillates that include, for example, paraffinic oils, napthenic oils, and combinations thereof. Specific examples of paraffinic oils can include mineral oil, petroleum jelly. The paraffinic and naphthenic oils disclosed herein preferably include a viscosity ranging from 0.5 to 2000 cP, 50 to 1500 cP, 200 to 1250 cP, 500 to 1000 cP, or 750 to 900 cP before being included within the shaving formulations. These organic, carbon based lubricants may be present in the disclosed shaving formulations at a concentration ranging 0 to 20 wt %, 3 to 16 wt %, 4 to 10 wt %, 5 to 8 wt %, or 6 to 8 wt % of the overall concentration of the shaving formulation.

Silicone based lubricants used within the shaving formulations may include one or more of volatile and/or non-volatile siloxanes. These siloxanes may include, but are not limited to, polydimethysiloxane (dimethicone) and derivatives thereof, cyclomethicone, or combinations thereof. These siloxanes may be present in the disclosed shaving formulations at a concentration ranging 0 to 20 wt %, 2 to 10 wt %, 2 to 8 wt %, 3 to 8 wt %, or 4 to 6 wt % of the overall concentration of the shaving formulation.

The above disclosed lubricants may be used in the disclosed formulation due to their lubricating and humectant properties. In addition, certain lubricants may act as defoamers, which aids in application to the user's skin by allowing for a more direct and focused application to a desired portion of the user's skin. These lubricants may further advantageously act as thickening agents thereby thickening the formulation and concurrently increasing viscosity of the formulation to a desired amount.

To further achieve the desired formulation viscosity, various thickening agents may be used. For example, these thickening agents may specifically include, but are not limited to, hydroxyethyl urea, carbomer, aluminum silicate, and starch or derivatives thereof (e.g., tapioca starch). In certain aspects, hydroxyethyl urea may be present in the shaving formulation at a concentration ranging from 0 to 20 wt %, from 1 to 15 wt %, from 3 to 12 wt %, from 4 to 10 wt %, or from 5 to 8 wt % of the overall formulation. In certain aspects, carbomer may be present in the shaving formulation at a concentration ranging from 0 to 20 wt %, from 1 to 10 wt %, from 2 to 8 wt %, from 2 to 6 wt %, or from 3 to 5 wt % of the overall formulation. In certain aspects, aluminum silicate may be present from 0 to 20 wt %, from 1 to 15 wt %, from 3 to 12 wt %, from 4 to 10 wt %, from 4 to 7 wt %, or from 4 to 6 wt % of the overall formulation. In certain aspects, starch (e.g., tapioca starch) may be present from 0 to 20 wt %, from 1 to 15 wt %, from 1 to 12 wt %, from 2 to 10 wt %, from 2 to 7 wt %, from 2 to 5 wt %, or from 2 to 4 wt % of the overall formulation.

In certain aspects, a triglyceride may be further included within the disclosed formulation. For example, the triglyceride may include glycerin or glycerol at a concentration from 1 to 12 wt %, preferably from 3 to 10 wt %, more preferably from 4 to 9 wt %, most preferably from 6 to 8 wt % of the overall formulation due to its humectant and skin moisturization properties. In addition, in various disclosed formulations, both glycerin (or glycerol) and hydroxyethyl urea may be present at a ratio of 1.5:1, 1.3:1, 1.2:1, 1:1, 1:1.1, 1:1.2, 1:1.3 of glycerin (or glycerol) to hydroxyethyl urea. Glycerin (or glycerol) and hydroxyethyl urea at the above disclosed concentrations with the disclosed ratios can synergistically enhance skin moisturizing and water retention (via humectant properties) to a user's skin.

To further aid in dispensability of the formulation by, for example, reducing overall formulation viscosity, water is included at a concentration of 1 to 70 wt %, 1 to 15 wt %, 1 to 10 wt %, 2 to 65 wt %, 2 to 8 wt %, 2 to 6 wt %, 3 to 60 wt %, or 3 to 5 wt % of the overall formulation. Within the formulation, water aids in solubilizing various components and further acts synergistically with the above mentioned humectants to moisturize and aid in moisture retention of the user's skin.

To further aid in solubility and dispensability, various organic solvents including one or more alcohols may be present within the disclosed shaving formulations. For example, cetyl alcohol, isopropyl alcohol, triethanolamine, phenoxyethanol, cetearyl alcohol, or any combination thereof may be present within the shaving formulation. In addition to adding in solubility, these alcohols may further act as anti-microbial agents and/or preservatives. Cetyl alcohol may be present within the formulation at a concentration ranging from 0 to 20 wt %, from 1 to 10 wt %, from 1 to 6 wt %, from 2 to 5 wt %, or from 2 to 4 wt %. Triethanolamine may be present within the formulation at a concentration ranging from 0 to 20 wt %, from 1 to 10 wt %, from 1 to 6 wt %, from 2 to 6 wt %, from 3 to 6 wt %, or from 3 to 5 wt %. Likewise, phenoxyethanol may be present within the formulation at a concentration ranging from 0 to 20 wt %, from 1 to 10 wt %, from 1 to 6 wt %, from 2 to 6 wt %, from 2 to 5 wt %, or from 2 to 4 wt %. Cetearyl alcohol may be present within the formulation at a concentration ranging from 0 to 20 wt %, from 1 to 10 wt %, from 1 to 6 wt %, from 2 to 6 wt %, from 1 to 3 wt %, or from 1 to 2 wt %.

Antimicrobial agents including various metal ions or metal salts, hydrogen peroxide, parabens, or a combination thereof may be included within the disclosed formulations. For example, the metal ions or metal salts having antimicrobial properties may include, for example, at least one of silver zeolite, silver zirconium phosphate, silver nitrate, silver thiosulfate, silver sulphadiazine, silver fusidate, copper zeolite, copper zirconium phosphate, copper nitrate, copper thiosulfate, copper sulphadiazine, copper fusidate, quaternary ammonium compounds (QAC), or any combination thereof. Other classes of silver-based antimicrobial agents may be used as well, for example a silver acetate, a silver bromide, a silver carbonate, a silver chlorate, a silver chloride, a silver citrate, a silver fluoride, a silver iodate, a silver lactate, a silver nitrate, a silver nitrite, a silver perchlorate or a silver sulfide. Parabens may include, for example, butylparaben, ehtylparaben, heptylparaben, metylparaben, or propylparaben. In certain aspects, propylparaben is present in the shaving formulation thereby enhancing the formulations antimicrobial properties and further acting as a preservative to lengthen the shelf-life of the disclosed formulation. One or more antimicrobial agents may be used within the formulation and either each antimicrobial agent or the combination of antimicrobial agents may be present at a concentration ranging from 0 to 20 wt %, 1 to 20 wt %, 2 to 15 wt %, 3 to 12 wt %, 4 to 10 wt %, 5 to 10 wt %, or 6 to 10 wt % of overall weight of the composition.

Additional additives such as preservatives, fragrances, colorants, or any combination thereof may be included within the disclosed formulations. In certain aspects, these additives may include, but are not limited to, preservatives (e.g., natural preservatives, synthetic preservatives, or combinations thereof) that include, but are not limited to, at least one of neem oil, sweet orange oil, Vitamin E, rosemary extract, grapefruit seed extract, potassium sorbate, benzylalcohol, disodium EDTA, tetrasodium EDTA, phenoxyethanol, propylene glycol, diazolidinyl urea, iodopropynyl, hydantoin, DMDM hydantoin, and any combination thereof. The disclosed formulation may include any one of these preservatives at a concentration of 0 to 20 wt %, 1 to 20 wt %, 2 to 18 wt %, 3 to 13 wt %, 4 to 13 wt %, 5 to 10 wt %, or 6 to 10 wt % of overall weight of the composition, or alternatively, the total amount of all preservatives in the formulation may include 0 to 20 wt %, 1 to 20 wt %, 2 to 18 wt %, 3 to 13 wt %, 4 to 13 wt %, 5 to 10 wt %, or 6 to 10 wt % of overall weight of the composition. In certain aspects, one or more fragrances may be included within the formulation at a concentration ranging from 0 to 8 wt %, 1 to 8 wt %, 2 to 7 wt %, 2 to 6 wt %, 2 to 5 wt %, 2 to 4 wt %, or 3 to 5 wt % of overall weight of the composition. In certain aspects, one or more colorants may be included within the formulation to achieve a desired color at a concentration ranging from 0 to 5 wt %, 1 to 5 wt %, 1 to 4 wt %, 1 to 3 wt %, 1 to 2 wt %, 2 to 4 wt %, or 2 to 3 wt % of overall weight of the composition.

The disclosed shaving formulations preferably soften, relax, and lubricate the skin and hair upon application to the user. These properties allow for a quick, easy shave while reducing or inhibiting the occurrence of knicks and cuts while shaving—often encountered problems with traditional shaving formulations. Also, unlike most conventional formulations that require a thick application layer of shaving formulation to the face or desired part to be shaved, the disclosed shaving formulation requires very little of the disclosed formulation to be applied to the user's skin/body hair while also achieving a fast, smooth, lubricating shave.

Also disclosed is a method of dispensing the disclosed shaving formulation by:
  (a) providing a spray pump bottle or a container having an atomizing head that contains the shaving formulation within the respective bottle or container;
  (b) dispensing the shaving formulation onto a desired surface (e.g., the face, legs, or other desired body part); and
  (c) removing the shaving formulation from the desired surface by shaving the desired surface with a razor.

In certain aspects, the spray pump bottle is configured to spray a mist.

Figure 2:
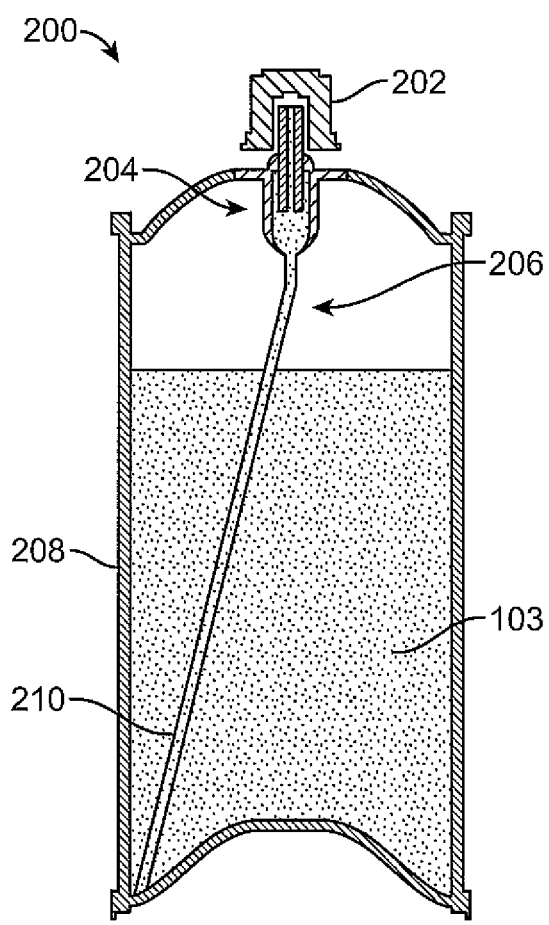
FIG. 2 depicts a container equipped with an atomizing head that is configured to apply the shaving formulation by spraying an aerosol.

Also disclosed is a container configured for dispensing a mist or aerosol, the container including a reservoir containing a shaving formulation having (a) from 5 to 60 wt % of at least one fatty acid or salt thereof; (b) at least one of sesame oil from 2 to 20 wt %, olive oil from 0 to 10 wt %, sandalwood oil from 0 to 10 wt %, broccoli seed oil from 0 to 10 wt %, or a combination thereof; (c) 1 to 10 wt % water; and (d) 0 to 20 wt % petroleum based lubricant, 0 to 20 wt % of a silicone based lubricant, 0 to 5 wt % fragrance, 0 to 5 wt % preservative, 0 to 30 wt % alcohol, 0 to 10 wt % thickeners, and 0 to 5 wt % antimicrobial agent; and a nozzle that is fluidly connected to the reservoir, the nozzle adapted for dispensing the shaving formulation as mist or aerosol. For example, FIG. 1 depicts spray bottle 100 having a reservoir filled with the disclosed formulation and a spray nozzle attached thereto and in fluid communication with the reservoir. Spray bottle 100 is configured to dispense the shaving formulation as a mist onto a desired bodypart. In certain aspects, spray bottle 100 includes a pump that draws liquid 103 (i.e., the shaving formulation)) from reservoir 102 up a siphon tube (not shown) from the reservoir and forces it through a nozzle. Depending on the sprayer, the nozzle of spray bottle 100 may or may not be adjustable, so as to select between squirting a stream or mist. FIG. 2 depicts container 200 equipped with an atomizing head 202, reservoir 208, optional propellant 206, valve, 204, shaving formulation 101, and a tube 210 allowing for fluid communication between the reservoir and atomizing head. Container 200 preferably includes the disclosed shaving formulation 101 and a propellant 206 thereby allowing for an aerosol form of the shaving formulation to be dispensed from the atomizing head of container 200. In certain aspects, the disclosed formulations may be further packaged for example, in moisture resistant, hermetically sealed packaging that may be repeatedly opened and closed. In the alternative, this packaging may contain a single use amount of the disclosed formulation.

EXAMPLES

The following examples provide those of ordinary skill in the art with a complete disclosure and description of how the compounds, compositions, and methods described and claimed herein are made and evaluated. These examples are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process.

Example 1

| Ingredient | Amount (Wt %) |
| --- | --- |
| Sesame oil | 8% |
| Isopropyl Alcohol | 7% |
| Petrolatum | 7% |
| Isopropyl Isostearate | 8% |
| Glycol Stearate | 8% |
| Glycerin | 7% |
| Hydroxyethyl Urea | 6% |
| Dimethicone | 5% |
| Aluminium Silicate | 5% |
| Hydrogen Peroxide | 4% |
| Stearic Acid | 4% |
| Isopropyl Myristate | 5% |
| Carbomer | 4% |
| Triethanolamine | 4% |
| Water | 3% |
| Tapioca Starch | 3% |
| Cetyl Alcohol | 3% |
| Hydantoin | 3% |
| Propylparaben | 3% |
| Phenoxyethanol | 3% |
| Total | 100% |

The ingredients of Example 1 are mixed and heated to produce a homogeneous, aqueous blend and are then placed into the spray bottles and containers disclosed above for dispensing from a spray pump bottle or a container with an atomizing head.

Example 2

| Ingredient | Amount (Wt %) |
| --- | --- |
| Olive oil | 8% |
| Isopropyl Alcohol | 7% |
| Petrolatum | 7% |
| Isopropyl Isostearate | 8% |
| Glycol Stearate | 8% |
| Glycerin | 7% |
| Hydroxyethyl Urea | 6% |
| Dimethicone | 5% |
| Aluminium Silicate | 5% |
| Hydrogen Peroxide | 4% |
| Stearic Acid | 4% |
| Isopropyl Myristate | 5% |
| Carbomer | 4% |
| Triethanolamine | 4% |
| Water | 3% |
| Tapioca Starch | 3% |
| Cetyl Alcohol | 3% |
| Hydantoin | 3% |
| Propylparaben | 3% |
| Phenoxyethanol | 3% |
| Total | 100% |

The ingredients of Example 2 are mixed and heated to produce a homogeneous, aqueous blend and are then placed into the spray bottles and containers disclosed above for dispensing from a spray pump bottle or a container with an atomizing head.

Example 3

| Ingredient | Amount (Wt %) |
| --- | --- |
| Sandalwood oil | 8% |
| Isopropyl Alcohol | 7% |
| Petrolatum | 7% |
| Isopropyl Isostearate | 8% |
| Glycol Stearate | 8% |
| Glycerin | 7% |
| Hydroxyethyl Urea | 6% |
| Dimethicone | 5% |
| Aluminium Silicate | 5% |
| Hydrogen Peroxide | 4% |
| Stearic Acid | 4% |
| Isopropyl Myristate | 5% |
| Carbomer | 4% |
| Triethanolamine | 4% |
| Water | 3% |
| Tapioca Starch | 3% |
| Cetyl Alcohol | 3% |
| Hydantoin | 3% |
| Propylparaben | 3% |
| Phenoxyethanol | 3% |
| Total | 100% |

The ingredients of Example 3 are mixed and heated to produce a homogeneous, aqueous blend and are then placed into the spray bottles and containers disclosed above for dispensing from a spray pump bottle or a container with an atomizing head.

Example 4

| Ingredient | Amount (Wt %) |
|---|---|
| Water | 56% |
| Sesame Oil | 6.5% |
| White Petroleum Oil | 3.0% |
| Glycerin | 3.0% |
| Coconut Oil | 6.5% |
| Stearic Acid | 3.0% |
| Dimethicone | 1.5% |
| Hydrogen Peroxide | 0.5% |
| Isopropyl Alcohol | 2.0% |
| Isopropyl Isostearate Acid | 1.0% |
| Broccoli Seed Oil | 2.0% |
| Glyceryl Stearate | 3.0% |
| Tapioca Starch | 1.0% |
| Olive Oil | 3.0% |
| Phenoxyethanol | 1.0% |
| Disodium EDTA | 1.0% |
| Triethanolamine | 2.0% |
| Isopropyl Myristate | 1.0% |
| DMDM hydantoin | 2.0% |
| Cetearyl Alcohol | 1.0% |
| Total | 100% |

The ingredients of Example 4 are mixed and heated to produce a homogeneous, aqueous blend and are then placed into the spray bottles and containers disclosed above for dispensing from a spray pump bottle or a container with an atomizing head.

Example 5

| Ingredient | Amount (Wt %) |
|---|---|
| Water | 53% |
| Sesame Oil | 6.5% |
| White Petroleum Oil | 3.0% |
| Glycerin | 3.0% |
| Coconut Oil | 6.5% |
| Stearic Acid | 3.0% |
| Dimethicone | 1.5% |
| Hydrogen Peroxide | 0.5% |
| Isopropyl Alcohol | 2.0% |
| Isopropyl Isostearate Acid | 1.0% |
| Broccoli Seed Oil | 2.0% |
| Glyceryl Stearate | 3.0% |
| Tapioca Starch | 1.0% |
| Olive Oil | 6.0% |
| Phenoxyethanol | 1.0% |
| Disodium EDTA | 1.0% |
| Triethanolamine | 2.0% |
| Isopropyl Myristate | 1.0% |
| DMDM hydantoin | 2.0% |
| Cetearyl Alcohol | 1.0% |
| Total | 100% |

The ingredients of Example 5 are mixed and heated to produce a homogeneous, aqueous blend and are then placed into the spray bottles and containers disclosed above for dispensing from a spray pump bottle or a container with an atomizing head.

Example 6

| Ingredient | Amount (Wt %) |
|---|---|
| Water | 51.5% |
| Glycerin | 7% |
| Petroleum | 7% |
| Coconut oil | 7% |
| Sesame oil | 7% |
| Olive oil | 3% |
| Broccoli seed oil | 3% |
| Steric acid | 1.5% |
| Hydrogen peroxide | 2% |
| Isopropyl alcohol | 1% |
| PEG-100 Stearate | 1% |
| Dimethicone | 1.5% |
| Isopropyl Isostearate | 1% |
| Hydroxyethyl urea | 1% |
| Tapioca starch | 1% |
| Cetyl alcohol | 1% |
| Glyceryl stearate | 1% |
| Magnesium aluminum silicate | 0.5% |
| Isopropyl myristate | 0.8% |
| Carbomer | 0.3% |
| Cedrol | 0.2% |
| Triethanolamine | 0.2% |
| Disodium EDTA | 0.1% |
| Phenoxyethanol | 0.1% |
| Methylparaben | 0.1% |
| DMDM hydratoin | 0.2% |
| Total | 100% |

The ingredients of Example 6 are mixed and heated to produce a homogeneous, aqueous blend and are then placed into the spray bottles and containers disclosed above for dispensing from a spray pump bottle or a container with an atomizing head.

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A sprayable shaving formulation comprising:
    (a) fatty acids or salts thereof at a concentration from 5 to 60 wt % of the sprayable shaving formulation; the fatty acids or salt thereof at least including glycerin at a concentration of 4 to 9 wt % of the spravable shaving formulation, isopropyl isostearate ranging from 1 to 15 wt % of the sprayable shaving formulation, isopropyl myristate ranging from 1 to 60 wt % of the sprayable shaving formulation,glvcervl stearate ranging from 1 to 60 wt % of the spravable shaving formulation, and glycol stearate at a concentration ranging from 2 to 15 wt % of the sprayable shaving formulation;
    (b) at least four oils comprising sesame oil, broccoli seed oil, coconut oil, and olive oil, and optionally sandalwood oil; wherein the sesame oil ranges from 3 to 15 wt % of the sprayable shaving formulation, the broccoli seed oil ranges from 1 to 10 wt % of the sprayable shaving formulation, and the olive oil ranges from 1 to 10 wt % of the sprayable shaving formulation, and, when present, sandalwood oil ranges from 1 to 10 wt % of the sprayable shaving formulation;
    (c) water ranging from 3 to 60 wt % of the sprayable shaving formulation;
    (d) a petroleum based lubricant ranging from 3 to 20 wt % of the sprayable shaving formulation, (e) dimethicone ranging from 3 to 8 wt % of the sprayable shaving formulation, (f) fragrance ranging from 0 to 5 wt % of the sprayable shaving formulation, (g) a preservative ranging from 0 to 5 wt % of the sprayable shaving formulation, (h) disodium EDTA or tetrasodium EDTA at a concentration ranging from 1 to 20 wt % of the sprayable shaving formulation, (i) plurality of alcohols that include at least triethanolamine at a concentration ranging from 1 to wt 10% of the shaving formulation, cetyl alcohol at a concentration ranging from 1 to 10 wt % of the sprayable shaving formulation, cetearyl alcohol at a concentration ranging from 1 to 10 wt % of the sprayable shaving formulation, phenoxyethanol at a concentration ranging from 1 to 10 wt % of the sprayable shaving formulation, (j) a tapioca starch as a thickener ranging from 1 to 3 wt % of the sprayable shaving formulation, and (k) an antimicrobial agent ranging from 0 to 5 wt % of the sprayable shaving formulation;

wherein the total weight percent of the sprayable shaving formulation is 100%, and, the sprayable shaving formulation has a viscosity for dispensing the sprayable shaving formulation as a mist from a spray pump bottle or an atomizing head in fluid communication with a container containing the sprayable shaving formulation at a temperature ranging from 65° F. to 100° F.

2. The sprayable shaving formulation of claim 1, wherein the formulation has a viscosity ranging from 3 to 75 cP.

3. The sprayable shaving formulation of claim 2, wherein sesame oil is present in the sprayable shaving formulation at a concentration ranging from 4 to 12 wt % of the sprayable shaving formulation.

4. The sprayable shaving formulation of claim 3, wherein broccoli seed oil is present in the sprayable shaving formulation at a concentration ranging from 2 to 8 wt % of the sprayable shaving formulation.

5. The sprayable shaving formulation of claim 4, wherein olive oil is present in the sprayable shaving formulation at a concentration ranging from 4 to 12 wt % of the sprayable shaving formulation.

6. The sprayable shaving formulation of claim 5, wherein sandalwood oil is present in the sprayable shaving formulation at a concentration ranging from 2 to 9 wt % of the sprayable shaving formulation.

7. A method of dispensing a sprayable shaving formulation comprising:

(a) dispensing the sprayable shaving formulation from a spray pump bottle or from an atomizing head in fluid communication with a container containing the sprayable shaving formulation, wherein:

the sprayable shaving formulation has viscosity of 3 to 50 cP at a temperature ranging from 65° F. to 100° F. and comprise;

(i) fatty acids or salts thereof at a. concentration of up to 60 wt % of the sprayable shaving formulation; the fatty acids or salt thereof in least including glycerin at a concentration of 4 to 9 wt % of the sprayable shaving formulation, isopropyl isostearate ranging from 1 to 15 wt % of the sprayable shaving formulation, isopropyl myristate ranging from 1 to 60 wt % of the sprayable shaving formulation, glyceryl stearate ranging from 1 to 60 wt % of the sprayable shaving formulation, and glycol stearate at a concentration ranging from 2 to 15 wt % of the sprayable shaving formulation;

(ii) at least four oils comprising sesame oil, broccoli seed oil, coconut oil, and olive oil, and optionally sandalwood oil, wherein the sesame oil ranges from 3 to 15 wt % of the sprayable shaving formulation, and the olive oil ranges from 1 to 10 wt % of the sprayable shaving formulation Oil, and, when present, sandalwood oil ranges from 1 to 10 wt % of the sprayable shaving formulation;

(iv) a petroleum based lubricant ranging from 3 to 20 wt % of the sprayable shaving formulation, (v) dimethicone ranging from 3 to 8 wt % of the sprayable shaving formulation, (vi) fragrance ranging from 0 to 5 wt % of the sprayable shaving formulation, (vii) a preservative ranging from 0 to 5 wt % of the sprayable shaving formulation, (viii) disodium EDTA or tetrasodium EDTA at a concentration ranging from 1 to 20 wt % of the sprayable shaving formulation, (ix) plurality of alcohols that include at least triethanolamine at a concentration ranging from 1 to wt 10% of the shaving formulation, cetyl alcohol at a concentration ranging from 1 to 10 wt % of the sprayable shaving formulation, cetearyl alcohol at a concentration ranging from 1 to 10 wt % of the sprayable shaving formulation, phenoxyethanol at a concentration ranging from 1 to 10 wt % of the sprayable shaving formulation, (x) a tapioca starch as a thickener ranging from 1 to 3 wt % of the sprayable shaving formulation, and (xi) an antimicrobial agent ranging from 0 to 5 wt % of the sprayable shaving formulation;

wherein the total weight percent of the sprayable shaving formulation is 100%.

\* \* \* \* \*